US010357362B2

(12) United States Patent
Anderson et al.

(10) Patent No.: US 10,357,362 B2
(45) Date of Patent: Jul. 23, 2019

(54) VALVE DELIVERY DEVICE WITH A PIEZOCHROMATIC FEEDBACK INDICATOR AND METHODS OF USE

(71) Applicant: Medtronic Vascular, Inc., Santa Rosa, CA (US)

(72) Inventors: Marc Anderson, Ballybrit (IE); Patrick Griffin, Ballybrit (IE); Caroline Hopkins, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 198 days.

(21) Appl. No.: 15/334,318

(22) Filed: Oct. 26, 2016

(65) Prior Publication Data

US 2017/0165063 A1  Jun. 15, 2017

Related U.S. Application Data

(60) Provisional application No. 62/264,955, filed on Dec. 9, 2015.

(51) Int. Cl.
*A61F 2/24* (2006.01)

(52) U.S. Cl.
CPC .......... *A61F 2/2436* (2013.01); *A61F 2/2427* (2013.01); *A61F 2210/00* (2013.01); *A61F 2250/009* (2013.01); *A61F 2250/0096* (2013.01)

(58) Field of Classification Search
CPC ............ A61F 2/2436; A61F 2002/9534; A61F 2210/00; A61F 2250/0096; A61F 2/2427; A61F 2/2433; A61F 2/95; A61M 25/104; A61M 2025/0008

USPC ............................... 606/194; 623/1.11, 2.11
See application file for complete search history.

(56) References Cited

U.S. PATENT DOCUMENTS

| 5,385,606 | A  |   | 1/1995  | Kowanko |             |
|-----------|----|---|---------|---------|-------------|
| 5,980,485 | A  | * | 11/1999 | Grantz  | A61M 25/10  |
|           |    |   |         |         | 604/96.01   |
| 6,310,036 | B1 |   | 10/2001 | Browdie |             |
| 6,645,240 | B2 |   | 11/2003 | Yee     |             |
| 7,632,298 | B2 |   | 12/2009 | Hijlkema et al. |    |
| 8,579,963 | B2 |   | 11/2013 | Tabor   |             |

(Continued)

FOREIGN PATENT DOCUMENTS

| WO | WO2007/134066 | 11/2007 |
| WO | WO2012/032147 | 3/2012  |
| WO | WO2012/125736 | 9/2012  |

OTHER PUBLICATIONS

PCT/US2016/067649, The International Search Report and the Written Opinion of the International Searching Authority, dated Apr. 19, 2017.

*Primary Examiner* — Katherine M Shi

(57) ABSTRACT

Heart valve delivery systems and methods for providing a clinician with feedback during a stented prosthetic heart valve delivery procedure. Feedback is provided using piezochromatic indicators incorporated into elements of the delivery device, such as the handle assembly, shaft assembly and capsule to indicate when detrimental forces, or forces nearing those that are detrimental, are being applied to the delivery device during the prosthetic heart valve loading, delivery or deployment procedure. Other embodiments incorporate a feedback indicator to indicate that a delivery device has previously been used and is not in a new condition.

10 Claims, 8 Drawing Sheets

(56) References Cited

U.S. PATENT DOCUMENTS

| | | | |
|---|---|---|---|
| 2003/0216732 A1* | 11/2003 | Truckai | A61B 18/14 606/49 |
| 2005/0080474 A1 | 4/2005 | Andreas et al. | |
| 2007/0233222 A1 | 10/2007 | Roeder et al. | |
| 2009/0093876 A1 | 4/2009 | Nitzan et al. | |
| 2010/0100167 A1 | 4/2010 | Bortlein et al. | |
| 2010/0198346 A1* | 8/2010 | Keogh | A61N 7/02 623/2.11 |
| 2011/0251683 A1* | 10/2011 | Tabor | A61F 2/2436 623/2.11 |
| 2012/0101515 A1* | 4/2012 | Barbod | A61M 25/104 606/194 |
| 2013/0060329 A1 | 3/2013 | Agnew et al. | |
| 2014/0039610 A1* | 2/2014 | Yeung | A61F 2/2418 623/2.11 |

* cited by examiner

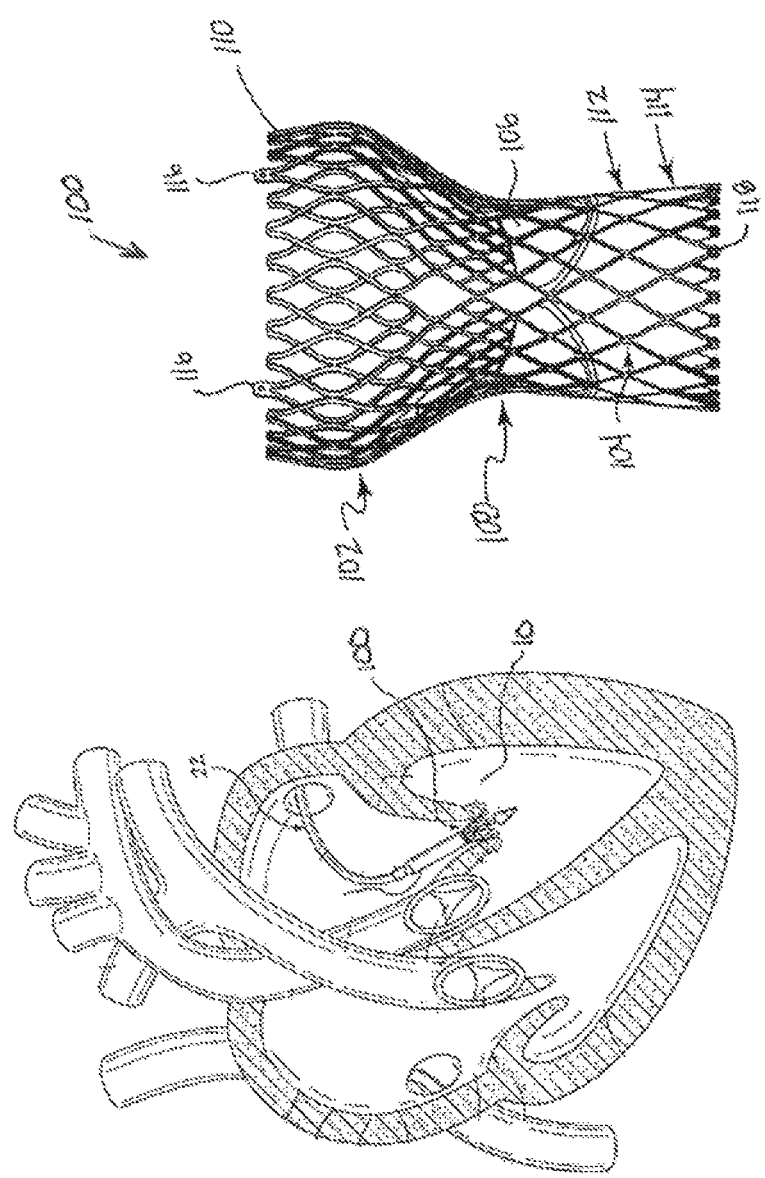

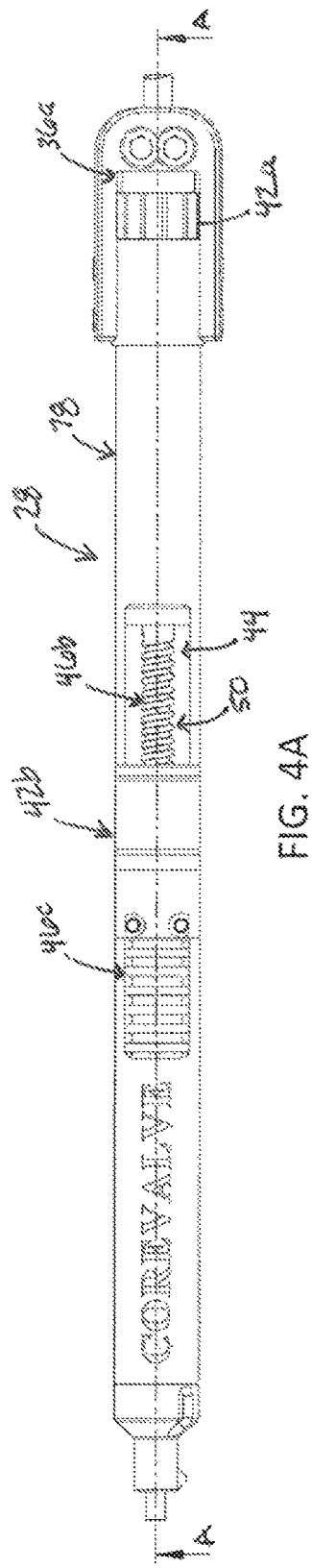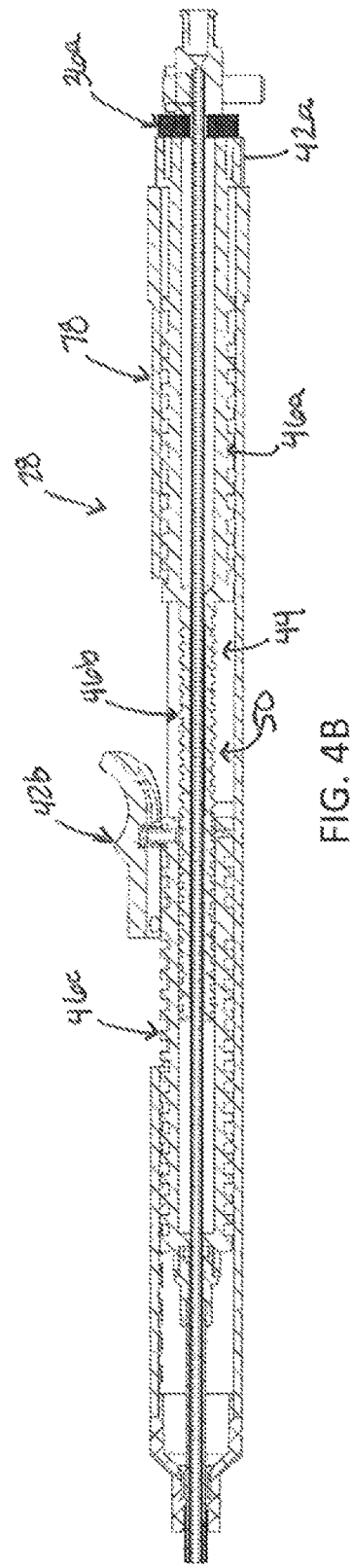
FIG. 4A
FIG. 4B

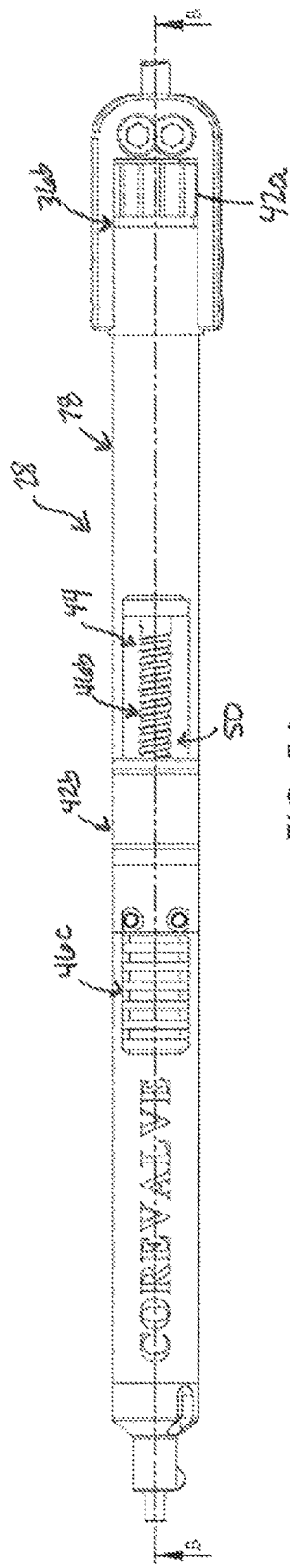
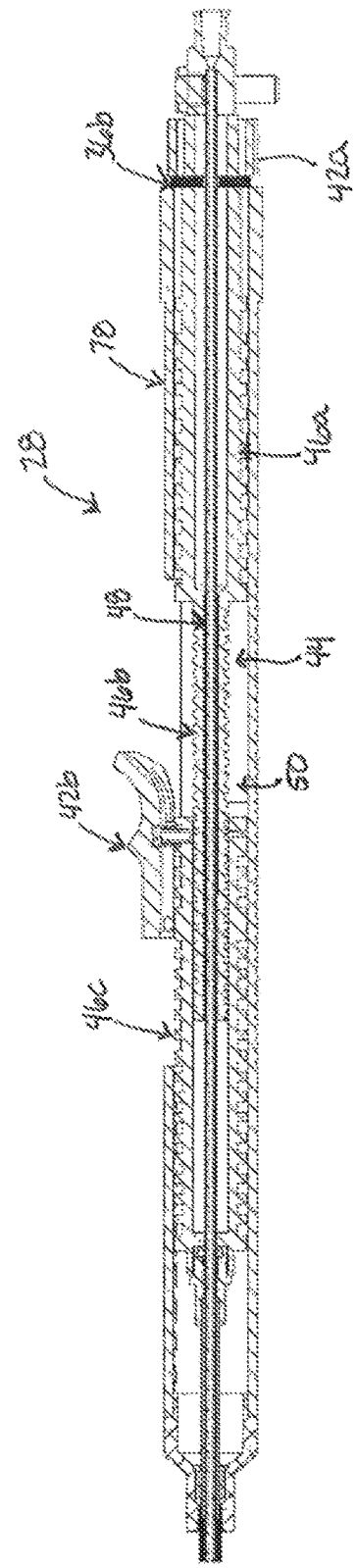
FIG. 5A
FIG. 5B

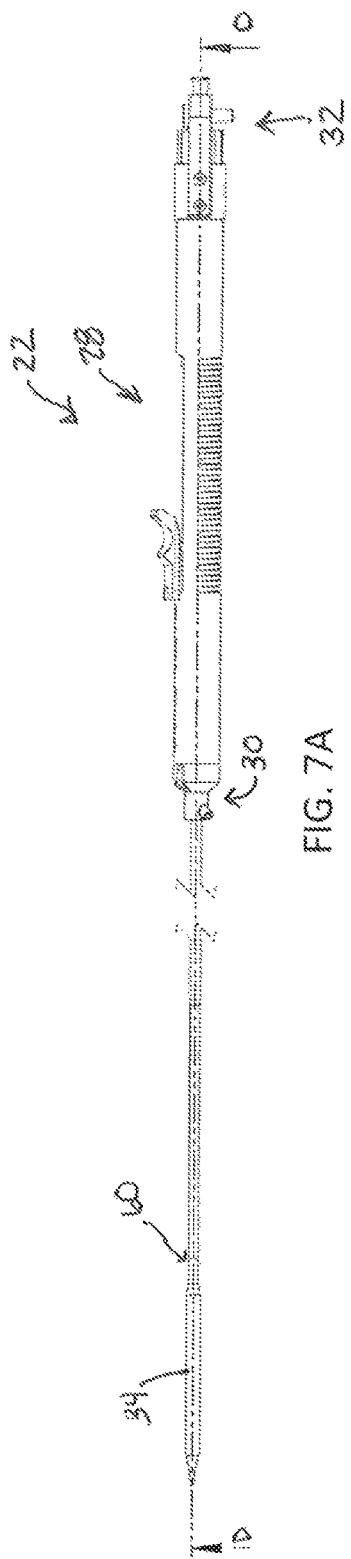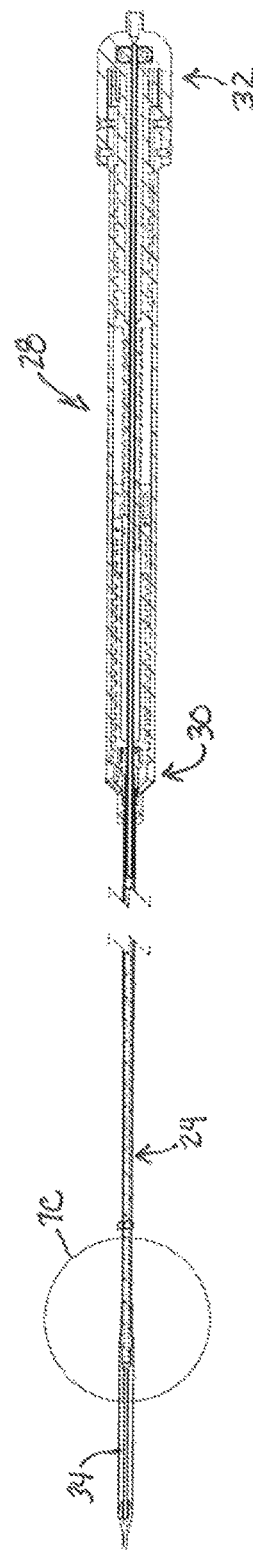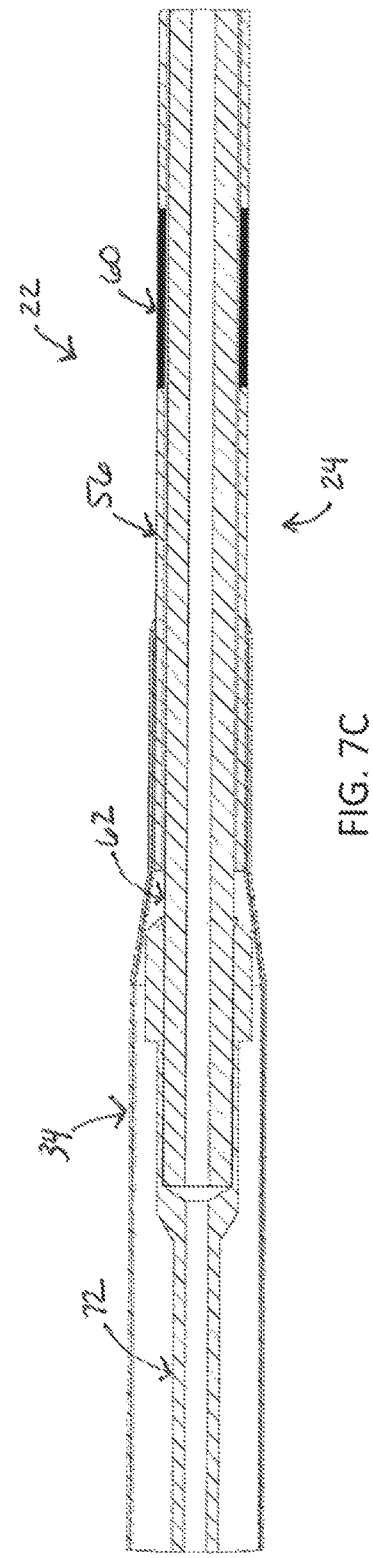
FIG. 7A
FIG. 7B
FIG. 7C

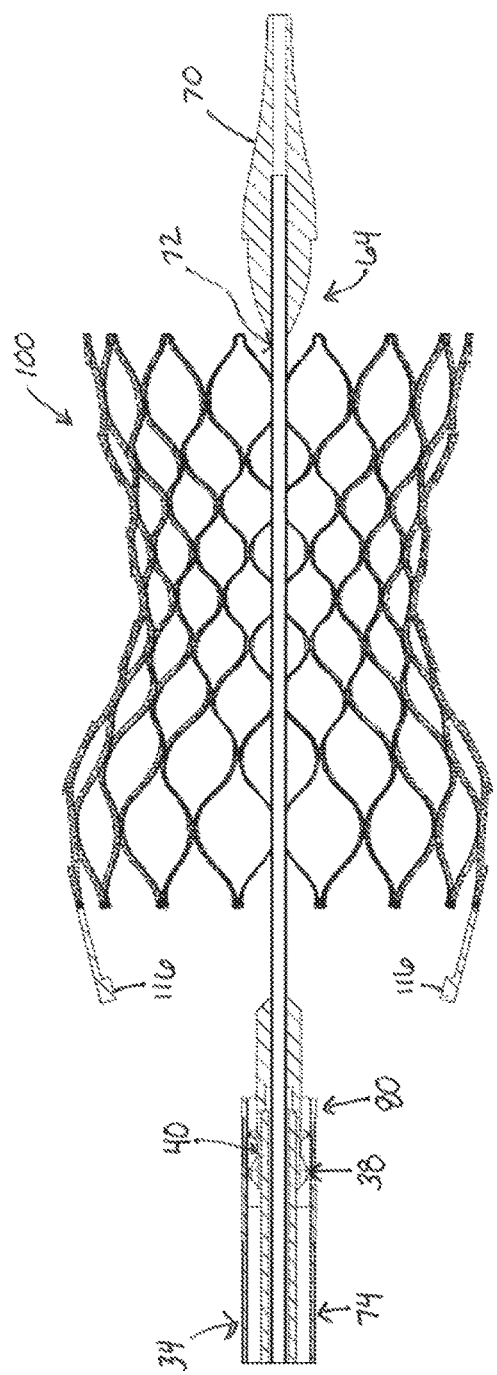
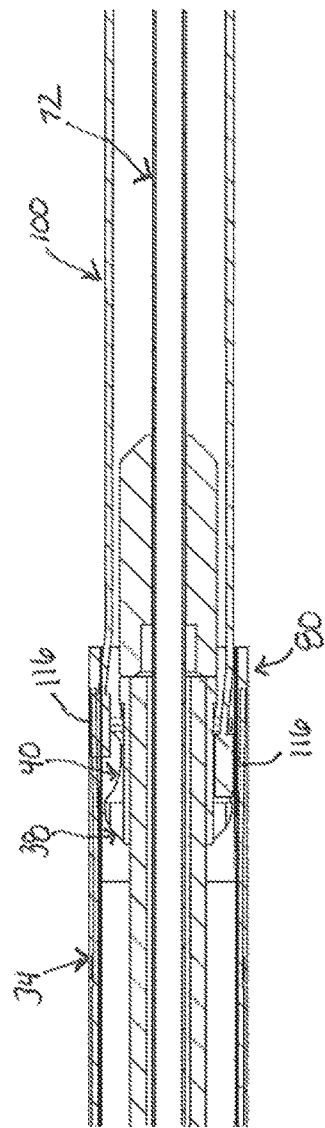
FIG. 8A
FIG. 8B

VALVE DELIVERY DEVICE WITH A PIEZOCHROMATIC FEEDBACK INDICATOR AND METHODS OF USE

CROSS-REFERENCE TO RELATED APPLICATIONS

This Non-Provisional Patent Application claims the benefit of the filing date of U.S. Provisional Patent Application Ser. No. 62/264,955, filed Dec. 9, 2015, entitled "Valve Delivery Device with a Piezochromatic Feedback Indicator and Methods of Use," which is herein incorporated by reference.

BACKGROUND

The present disclosure relates to delivery devices for delivering a prosthetic heart valve. More particularly, it relates to prosthetic heart valve delivery devices providing clinician feedback during the valve delivery procedure.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of a prosthetic heart valve or prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

The actual shape and configuration of any particular transcatheter prosthetic heart valve is dependent, at least to some extent, upon the valve being replaced or repaired (e.g., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Taken in combination, these design features can give rise to delivery obstacles. For example, when compressed and constrained within the delivery device's outer sheath capsule, a self-expanding stent frame will exert significant radial forces on the capsule. Thus, the capsule must have a robust construction, capable of statically resisting the applied force. However, the capsule, as well as other portions of the outer sheath, must also be sufficiently flexible to traverse the tortuous path leading to the native valve annulus site. As a point of reference, the preferred delivery approach oftentimes includes one or more significant bends or turns. In many instances, the native anatomy creates the "tight" or small radius of curvature bends; as the capsule (or other components of the delivery device) comes into atraumatic contact with the native anatomy, the native anatomy naturally assists in "forcing" the outer sheath (including the capsule) to the necessary shape. A retrograde approach to the aortic valve is but one example, where contact with the native anatomy assists in directing the delivery device about the significant curvature of the aortic arch.

It is imperative that the stented prosthetic heart valve be accurately positioned relative to the native valve immediately prior to deployment from the catheter as successful implantation requires the transcatheter prosthetic heart valve intimately lodge and seal against the native tissue. If the prosthesis is incorrectly positioned relative to the native tissue, serious complications can result as the deployed device can leak (such as paravalvular leakage) and may even dislodge from the implantation site. In an effort to enhance the accuracy of the prosthetic heart valve placement, imaging technology has been utilized to assist a clinician in better evaluating the position of the transcatheter prosthetic heart valve immediately prior to deployment and implantation.

Although there have been multiple advances in transcatheter prosthetic heart valves and related delivery systems and techniques, there is a continuing need to provide different delivery systems capable of providing feedback information to the clinician. Various known methods of relaying such feedback to a clinician include mechanical and electromechanical sensors. Such known sensors are costly.

The present disclosure addresses problems and limitations with the related art.

SUMMARY

Various disclosed embodiments include a delivery device for delivery and deployment of a stented prosthetic heart valve. The delivery device can include an outer sheath assembly, an inner shaft assembly and a handle assembly for actuation of the outer sheath assembly to deploy the valve. Other types of delivery devices for delivering the stented prosthetic heart valve to a native heart valve are also contemplated. Disclosed embodiments provide visual feedback to the clinician by way of one or more piezochromatic feedback indicators incorporated into at least one part of the delivery device. Feedback indicators disclosed herein include piezochromatic polymers comprising piezochromatic pigments. Such piezochromatic pigments change color when subjected to force such as pressure or strain. The piezochromatic pigments are incorporated into the feedback indicators, as desired for the particular delivery device, to change color when detrimental forces or forces nearing those that are detrimental, are being applied or have been applied to the delivery device.

In one embodiment, the delivery device includes at least one feedback indicator in a handle assembly, proximate actuation mechanisms, such as a knob and drive screw element, to monitor forces along the drive screw element. In another embodiment, one or more feedback indicators can be configured to provide an indication that a shaft of the delivery device is being stressed excessively during the delivery procedure. In further embodiments, one or more feedback indicators can be incorporated into a capsule of the delivery device to indicate when a stented prosthetic heart valve is misloaded within the capsule. In yet further embodiments, one or more feedback indicators can be configured to indicate that the delivery device has previously been used and/or whether shipping and handling damage has occurred. Additional embodiments provide one or more feedback indicators for the purpose of identifying a genuine delivery device as compared to a counterfeit delivery device.

Methods of using the disclosed devices and providing feedback to a clinician are also disclosed.

BRIEF DESCRIPTION OF THE DRAWINGS

FIG. 1 illustrates an exemplary transcatheter stented prosthetic heart valve delivery procedure.

FIG. 2 illustrates an exemplary stented prosthetic heart valve useful with systems, devices and methods of the present disclosure and in a normal, expanded condition.

FIG. 4A is a partial, side view of the delivery device of FIG. 3.

FIG. 4B is a partial, cross-sectional view of the delivery device of FIGS. 3-4A as viewed along line A-A; the delivery device having a feedback indicator proximal to an actuating knob.

FIG. 5A is a partial, side view of a delivery device, largely similar to that of FIGS. 3-4B, but having a feedback indicator distal to the actuating knob.

FIG. 5B is a partial, cross-sectional view of the delivery device of FIG. 5A as viewed along line B-B.

FIG. 7A is a side view of a delivery device of FIG. 3 having one feedback indicator incorporated into an outer sheath.

FIG. 7B is a partial, cross-sectional view of the delivery device of FIG. 7A as viewed along line D-D.

FIG. 7C is an enlarged view of Section 7C of FIG. 7B.

FIG. 8A is a partial, schematic view of the third feedback indicator, which is integrated into a capsule of the delivery device of FIGS. 3-7C, the figure also illustrating a paddle of the stented prosthetic heart valve in a first stage as it is loaded within the capsule of the delivery device.

FIG. 8B is a partial, schematic view of the delivery device of FIGS. 3-8A illustrating the stented prosthetic heart valve in a second stage as it is being loaded within the capsule of the delivery device; wherein the paddle is misplaced and is disengaged with a spindle of the delivery device.

DETAILED DESCRIPTION

Figure 3:
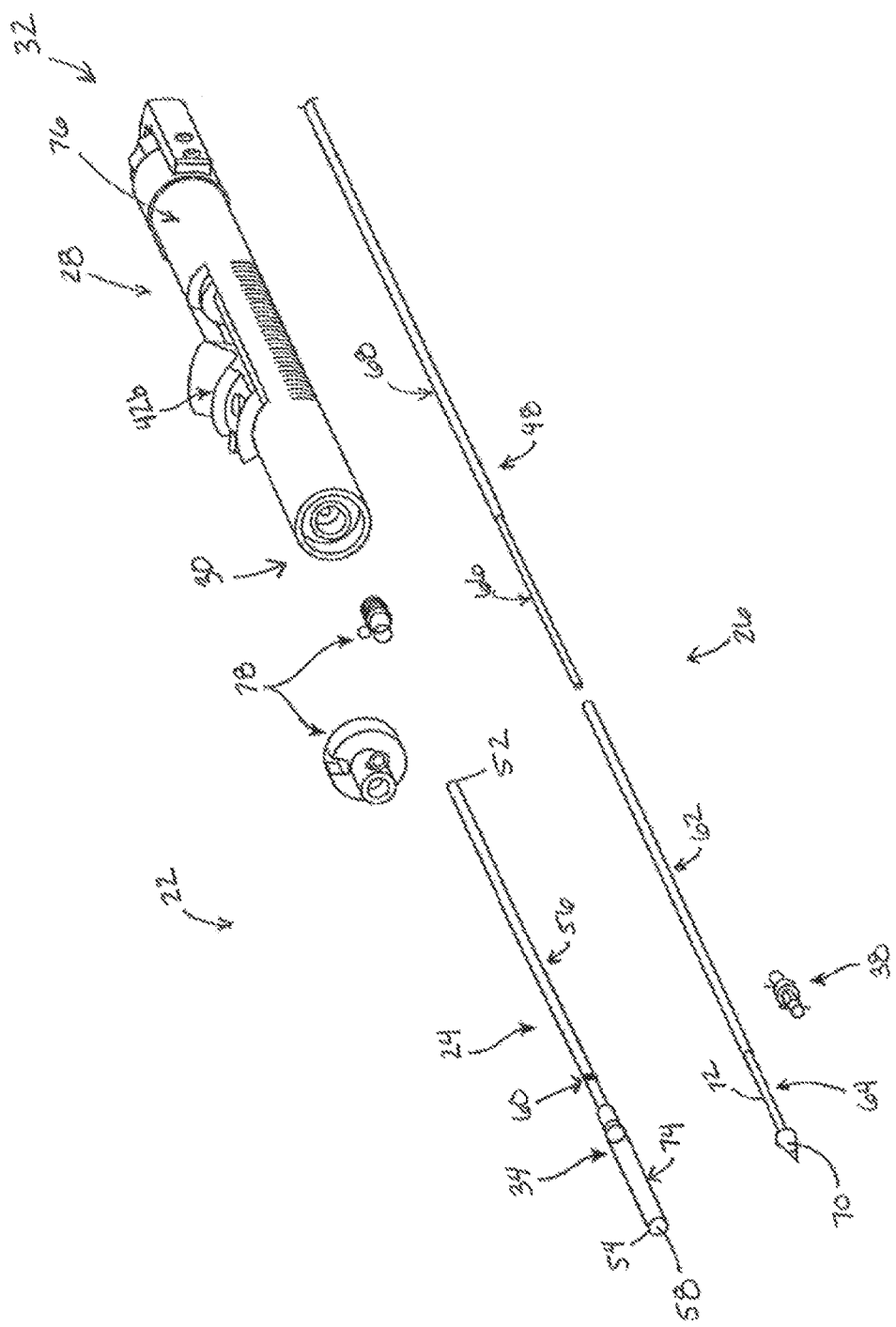
FIG. 3 is an exploded perspective view of the delivery device of FIG. 1 having feedback indicators.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from, or in a direction away from the clinician. "Proximal" and "proximally" are a position near or in a direction toward the clinician. As used herein, with reference to an implanted valve prosthesis, the terms "distal," "outlet," and "outflow" are understood to mean downstream to the direction of blood flow, and the terms "proximal," "inlet," or "inflow" are understood to mean upstream to the direction of blood flow. Although the present disclosure has been described with reference to preferred embodiments, workers skilled in the art will recognize that changes can be made in form and detail without departing from the spirit and scope of the present disclosure.

Various disclosed embodiments include a valve delivery device having one or more piezochromatic feedback indicators made of a piezochromatic polymer. Piezochromatic polymers are macromolecular materials containing piezochromatic pigments that change their absorption color in response to force, such as pressure or strain. The feedback indicators can be configured so that they change color when detrimental forces are applied to the delivery device, which can visually warn a clinician that the delivery device is being used improperly. Alternatively, the feedback indicators can be configured to indicate that the delivery device has previously been used and is not in new condition.

In various embodiments, the piezochromatic pigments are "reversible pigments," which means that they will change color upon the application of pressure set to a predetermined threshold and return to the pigment's original color when the pressure, strain, or other stress is reduced to below the predetermined threshold. In other various embodiments, the piezochromatic pigments are "memory pigments," meaning that the pigments are configured to change color at a predetermined threshold and this color change is generally maintained when the force is within a set pressure range (i.e. a color change will occur when the pressure reaches P2 and the change will remain when the pressure is in the range of P1-P2, where P1 is less than P2). Other suitable piezochromatic pigments may be of the type that are "irreversible pigments" and will change color under the effect of pressure meeting a predetermined threshold and the color will generally remain unchanged when the pressure is alleviated to any degree. Irreversible piezochromatic pigments are particularly useful as a feedback indicator to signal that the delivery device is in a "used condition" and are also useful to serve as a record of how a delivery device was used in a procedure. Irreversible piezochromatic pigments are also particularly useful for indicating shipping and handling damage.

As used herein, references to "force," "pressure," "load," "strain," and "stress" shall all be considered synonymous and generally reference forces being placed on the delivery device during a valve loading or delivery procedure. Such forces can include, but are not limited to, those forces disclosed below with respect to how the disclosed feedback indicators can be incorporated into various valve delivery devices. Although examples of detrimental force and misuse of the device are generally described, the disclosed embodiments are not intended to be limited for these specific purposes and conditions. The location and amount of force to be considered detrimental to, or a misuse of, the delivery device will depend on many variable aspects of the specific delivery device in which the feedback indicator(s) is incorporated. Furthermore, the embodiments disclosed herein can be configured to warn a clinician that the amount of force being exerted on the device is nearing a detrimental level but has not yet reached a level that is, in fact, detrimental.

FIGS. 1 and 3-8D illustrate a few non-limiting examples of how a delivery device 22 can be configured for percutaneously delivering a self-expandable prosthesis, such as a stented prosthetic heart valve 100, to a patient's defective heart valve 10. The delivery device 22 includes an outer or delivery sheath assembly 24, an inner shaft assembly 26, and a handle assembly 28 having a distal end 30 and a proximal end 32. The handle assembly 28 includes at least one piezochromatic feedback indicator 36a-b, the placement of which can vary, as will be discussed in further detail below. The delivery device 22 provides a loaded or delivery state in which a stented prosthetic heart valve 100 can be loaded over the inner shaft assembly 26 and is compressively retained within a capsule 34 of the delivery sheath assembly 24. For example, the inner shaft assembly 26 can include a valve retainer 38 which has a recess 40 configured to selectively receive corresponding feature(s) (e.g., paddles, posts, or eyelets) 116 that are provided with a frame 102 of the stented prosthetic heart valve 100. The delivery sheath assembly 24 can be manipulated to withdraw the capsule 34 proximally from over the stented prosthetic heart valve 100 via operation of the handle assembly 28, permitting the prosthesis to self-expand and partially release from the inner shaft assembly 26. With the exemplary embodiments illustrated, movement of the delivery sheath assembly 24 is controlled by rotating actuating knob 42a or another actuation mechanism 42b that subsequently drive screw element 44, which is comprised of external threads 46a-c. When the capsule 34 is retracted proximally beyond the valve retainer 38, the stented prosthetic heart valve 100 can be completely released or deployed from the delivery device 22.

At least one feedback indicator 36a-b can be incorporated into the handle assembly 28 at any place along the drive screw element 44, as desired. As illustrated in FIGS. 4A-4B, the feedback indicator 36a is secured onto a proximal tube 48 of the inner shaft assembly 26 and to the actuating knob 42a. As the actuating knob 42a is rotated (e.g., counter-clockwise), the capsule 34 is advanced and the drive screw element moves through an interior 50 of housing 76, pressing the actuating knob 42a against the feedback indicator 36a transmitting the full load to the feedback indicator 36a. In this embodiment, the feedback indicator 36a is generally disc-shaped and is exposed as compared to the interior 50 of the housing 76 so that it is visible to the clinician.

In other embodiments, as is generally illustrated in FIGS. 5A-5B, the feedback indicator 36b is secured onto the proximal tube 48 and is positioned distal to the actuating knob 42a. As the actuating knob 42a is rotated (e.g., clockwise), the capsule 34 is retracted and the drive screw element 44 moves through the interior 50 of the housing 76, pressing the actuating knob 42a against the feedback indicator 36b and transmitting the full load to the feedback indicator 36b. As with the previous embodiment, the feedback indicator 36b is generally disc-shaped and is exposed as compared to the interior 50 of the housing 76 so that it is visible to the clinician.

Figure 6A:
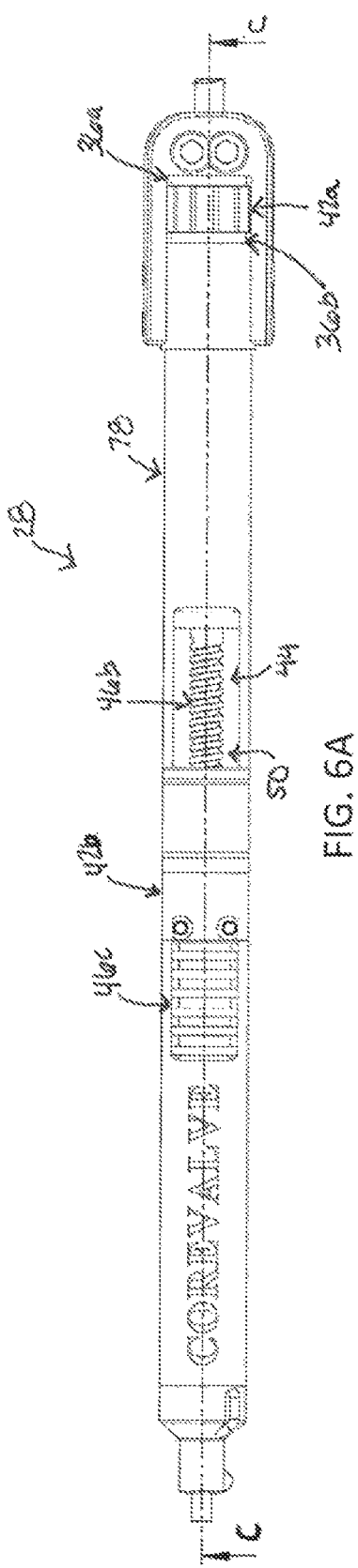
FIG. 6A is a partial, side view of a delivery device, largely similar to that of FIGS. 3-5B but having two feedback indicators, one proximal and one distal to the actuating knob.
Figure 6B:
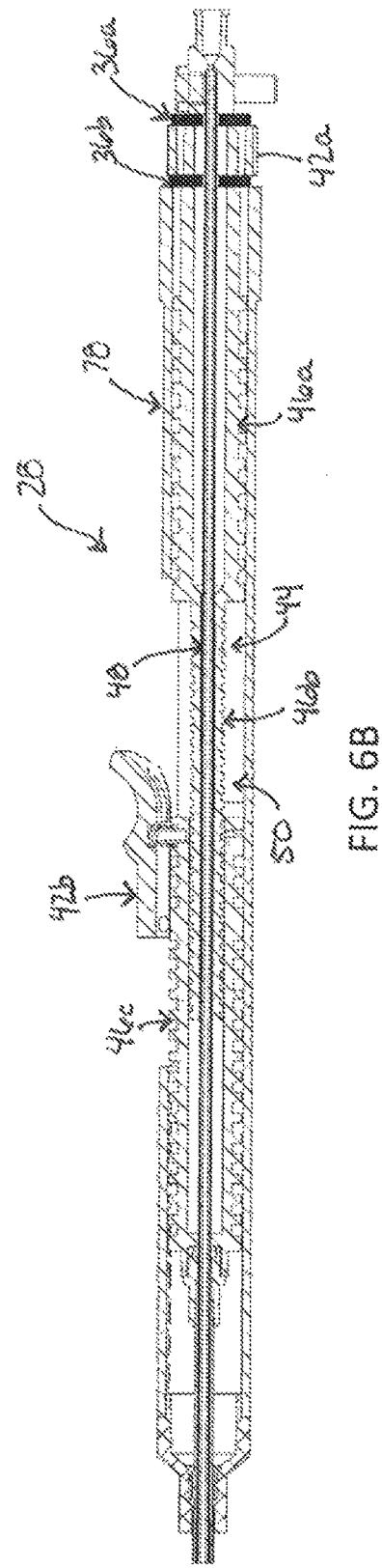
FIG. 6B is a partial, cross-sectional view of the delivery device of FIG. 6A as viewed along line C-C.
Figure 8C:
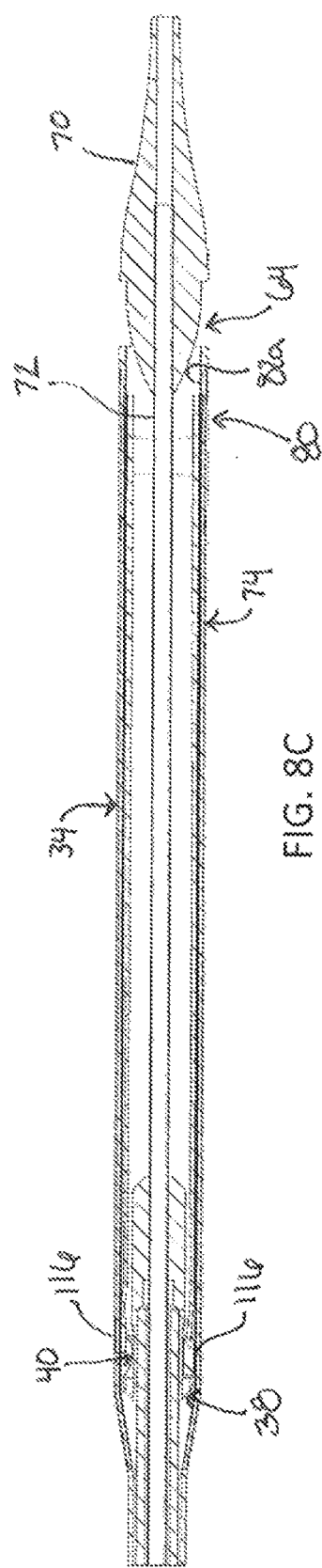
FIG. 8C is a partial, schematic view of the of the delivery device of FIGS. 3-8B illustrating the stented prosthetic heart valve in a third stage as it is misloaded within the capsule of the delivery device such that one paddle is applying pressure to an interior surface of the capsule.
Figure 8D:
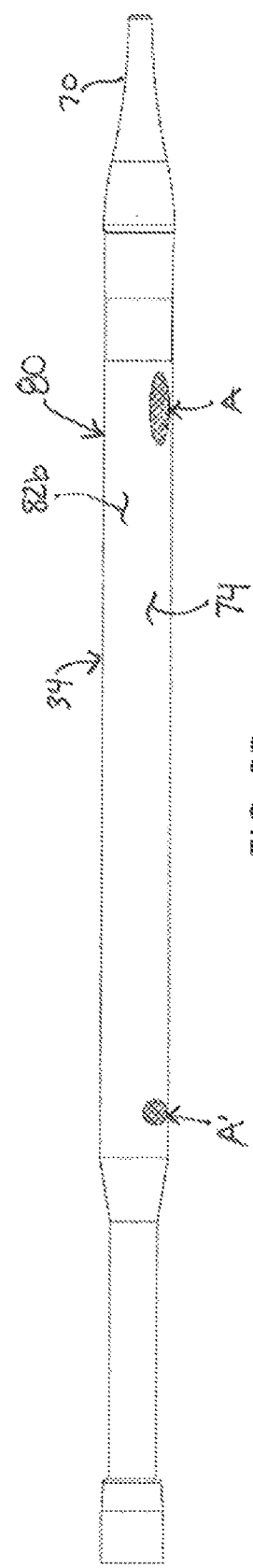
FIG. 8D is a partial, schematic view of the delivery device of FIGS. 3-8C illustrating that the pressure from a misplaced paddle on the capsule as shown in FIG. 8C has triggered a color change of the third feedback indicator to visually represent to a clinician that the stented prosthetic heart valve has been misloaded.

In addition, as is generally illustrated in FIGS. 6A-6B, the delivery device 22 can include two feedback indicators 36a, 36b, both proximal and distal to the actuating knob 44 for providing feedback to a clinician regarding excessive forces being placed on the delivery device 22 while advancing and retracting the capsule 34.

In some embodiments, the delivery sheath assembly 24 defines proximal and distal ends 52, 54, and includes the capsule 34 and an outer sheath 56. The delivery sheath assembly 24 can be akin to a catheter, defining a lumen 58 (referenced generally) that extends from the distal end 54, through the capsule 34, and through at least a portion of the outer sheath 56. The lumen 58 can be open at the proximal end 52 (e.g., the outer sheath 56 can be a tube). The capsule 34 extends distally from the outer sheath 56, and in some embodiments, has a more stiffened construction (as compared to a stiffness of the outer sheath 56) that exhibits sufficient radial or circumferential rigidity to overtly resist the expected expansive forces of the stented prosthetic heart valve 100 when compressed within the capsule 34. For example, the outer sheath 56 can be a polymer tube embedded with a metal braiding, whereas the capsule 34 includes a laser-cut or etched metal tube, wound braid, or coil that is optionally embedded within a polymer covering. Alternatively, the capsule 34 and the outer sheath 56 can have a more uniform or even homogenous construction (e.g., a continuous polymer tube). Regardless, the capsule 34 is constructed to compressively retain the stented prosthetic heart valve 100 at a predetermined diameter when loaded within the capsule 34, and the outer sheath 56 serves to connect the capsule 34 with the handle assembly 28. The outer sheath 56 (as well as the capsule 34) is constructed to be sufficiently flexible for passage through a patient's vasculature, yet exhibits sufficient longitudinal rigidity to effectuate the desired axial movement of the capsule 34. In other words, proximal retraction of the outer sheath 56 is directly transferred to the capsule 34 and causes proximal retraction of the capsule 34. In other embodiments, the outer sheath 56 is further configured to transmit a rotational force or movement onto the capsule 34. Such rotational force can be monitored with second feedback indicator 60.

As generally depicted in FIGS. 7A-7C, the delivery device 22 can alternatively or additionally include a second feedback indicator 60 provided at the outer sheath 56 proximate the capsule 34. Alternatively, the second feedback indicator 60 can be integrally incorporated into the material of the outer sheath 56 such that the entire outer sheath 56 serves as the second feedback indicator 60. The second feedback indicator 60 is configured, for example, to visually indicate when a detrimental amount of stretching of the outer sheath 56 has occurred. The second feedback indicator 60 is integrated into the outer sheath 56 such that it is in series with the load or pressure being applied to the outer sheath 56.

In embodiments, disclosed herein, the inner shaft assembly 26 can have various constructions appropriate for supporting the stented prosthetic heart valve 100 within the capsule 34. In some embodiments, the inner shaft assembly 26 includes the valve retainer 38, a proximal shaft or tube 48, and an intermediate shaft or tube 62. In general terms, the valve retainer 38 can be provided with, or assembled to, a distal retention member 64 and incorporates features for retaining the stented prosthetic heart valve 100 within the capsule 34. The intermediate tube 62 connects the distal retention member 64 to the proximal tube 48, with the proximal tube 48, in turn, coupling the inner shaft assembly 26 with the handle assembly 28. The inner shaft assembly 26 defines a continuous lumen sized to slidably receive an auxiliary component such as a guide wire (not shown).

The intermediate tube 62 may be formed of a reinforced flexible polymer material (e.g., Pebax, nylon) or a semi rigid polymer i.e. PEEK), and is sized to be slidably received within the delivery sheath assembly 24 and the shaft 56, in particular. The proximal tube 48 can include a leading portion 66 and a trailing portion 68. The leading portion 66 serves as a transition between the proximal and intermediate tubes 48, 62, and thus can be flexible tubing (e.g., Pebax, PU, Nylon PEEK) with a diameter slightly less than that of the intermediate tube 62. The trailing portion 68 can have a more rigid construction, configured for robust assembly with the handle assembly 28. For example, the trailing portion 68 can be a metal hypotube, although other constructions are also acceptable. In other embodiments, the proximal and intermediate tubes 48, 62 are integrally formed as a single, homogenous tube or shaft.

The distal retention member 64 can include a tip 70, a support tube 72, and the valve retainer 38. The tip 70 forms or defines a nose cone having a distally-tapering outer surface that is adapted to promote atraumatic contact with bodily tissue. The tip 70 can be fixed or slidable relative to the support tube 72. The support tube 72 extends proximally from the tip 70 and is configured to internally support a compressed, stented prosthetic heart valve generally disposed thereover (see also, FIG. 8A). The valve retainer 38 is mounted to the support tube 72 and generally has a hub-like construction. The valve retainer 38 forms or carries features, such as a recess 40, or raised feature (pin, boss), configured to selectively receive corresponding feature(s) provided with the stented prosthetic heart valve 100.

FIGS. 8A-8D schematically illustrates an additional or alternative feedback indicator 74 as incorporated into the capsule 34. The distal retention member 64 has a tip 70 and supports the stented prosthetic heart valve 100 with the assistance of valve retainer 38. The stented prosthetic heart valve 100 includes one or more paddles 116, which engage a corresponding area of the recess 40 in the valve retainer 38 that is secured over distal retention member 64. In securing the stented prosthetic heart valve 100 to the valve retainer 38, the paddles 116 may not be aligned properly or can disengage prior to completely loading the stented prosthetic heart valve 100 within the capsule 34. This is referred to as "misloading" the stented prosthetic heart valve 100. The capsule 34 is designed to incorporate the third feedback indicator 74 proximate a distal end 80 of the capsule 34. In the illustrated embodiment, the third feedback indicator 74 can be blended with a material of the capsule 34 at the time of manufacture and, thus, the third feedback indicator 74 can be integral with the capsule 34. In essence, the third feedback indicator 74 can be positioned anywhere in or on the capsule 34, as desired. In various embodiments, the third feedback indicator 74 and capsule 34 are arranged and configured such that when one or more of the paddles 116 is not properly engaged with the valve retainer 38, the respective paddle 116 will place pressure on an interior surface 82a of the capsule 34 to trigger the third feedback indicator 74 to change color. The change in color is thus visible on an exterior surface 82b on the capsule 34 (schematically illustrated at areas A, A' in FIG. 8D). The color change provides a visual indication or feedback to the clinician that the stented prosthetic heart valve 100 is not loaded properly within the capsule 34. It will be understood that the color change areas A, A' will vary depending on the piezochromatic pigments chosen and how such piezochromatic pigments are incorporated into the capsule 34. For example, if the stented prosthetic heart valve 100 is misloaded, area A would change color as the stented prosthetic heart valve 100 first enters the capsule 34. Area A' would only change colors once the misloaded stented prosthetic heart valve 100 reaches area A'. If the feedback indicator 74 includes reversible piezochromatic pigments, areas A and A' would likely not both be colored at the same time, as the pressure at area A would be alleviated by the time the stented prosthetic heart valve 100 is fully loaded. If the feedback indicator 74 is irreversible and integrated with the material of the capsule 34, there would likely be a line interconnecting areas A and A' indicating the path of the misplaced paddle 116 contacting the capsule 34. The disclosed third feedback indicator 74 is particularly beneficial to incorporate into delivery devices 22 having an opaque capsule 34 where it may otherwise be difficult to determine if the stented prosthetic heart valve 100 is misloaded within the capsule 34. The disclosed third feedback indicator 74 is also particularly beneficial to incorporate at the distal end of the capsule 34 so that a misloading of the stented prosthetic heart valve 100 is quickly indicated at the beginning of the process of loading the stented prosthetic heart valve 100.

Other placement and configuration of feedback indicators can be incorporated into the delivery device 22 as desired. For example, one or more feedback indicators, similar to feedback indicators 36a-b, 60, 74, can be configured to indicate when the delivery device 22 has been previously used. In this situation, the feedback indicator is non-reversible and will be configured to have a relatively low threshold such that any use of the delivery device 22 under normal, proper operating conditions will trigger a non-reversible color change. This embodiment is particularly useful in preventing the resale or reuse of used delivery devices.

Various features of the components 24-28 reflected in the figures and as described herein can be modified or replaced with differing structures and/or mechanisms. Thus, the present disclosure is in no way limited to the delivery sheath assembly 24, the inner shaft assembly 26, or the handle assembly 28 as shown and described herein. Any construction that generally facilitates delivery of a stented prosthetic heart valve (e.g., a self-expandable, a balloon-expandable, or a mechanically-expandable stented prosthetic heart valve) is acceptable. Furthermore, the delivery device 22 can optionally include additional components or features, such as a flush port assembly 78, a recapture sheath, a stability tube (not shown), etc. In addition, piezochromatic feedback indicators can also be incorporated into delivery devices configured for delivering stented prosthetic heart valves inserted transatrially or transeptally where entry may be done either percutaneously or in a minimally invasive technique on a beating heart in which access is through the side of the heart, or even delivery devices configured for access through an open heart valve replacement procedure.

The feedback indicators 36a-b, 60, 74 disclosed herein comprise piezochromatic polymers that can be produced, for example, by incorporating piezochromatic pigments in polymer materials such as Peba, Peek ABS, PU, polystyrene, PET-G or the like. Exemplary piezochromatic pigments can be obtained from OliKrom SAS Company, 16 Avenue Pey Berland, bâtiment ChemInnov, 33607 PESSAC, FRANCE. Suitable piezochromatic pigments can be of a wide range of colors and pigment particle sizes and also may be provided as either a dry powder or aqueous emulsion. In some embodiments, the piezochromatic polymer will include about 2% to about 3% piezochromatic pigment by weight. The piezochromatic pigments are selected in a manner such that the resultant feedback indicator 36a-b, 60, 74 will visually alert the clinician that a detrimental amount of force, as determined by the manufacturer of the delivery device 22, is being applied to at least one portion of the delivery device 22.

Delivery devices disclosed herein need not necessary include all three feedback indicators 36a-b, 60, 74. Furthermore, the disclosed feedback indicators 36a-b, 60, 74 are not intended to be limited to any specific shape, size, or area of placement on or within the delivery device 22. The disclosed feedback indicators 36a-b, 60, 74 are to be configured such that the feedback indicators 36a-b, 60, 74 are capable of visually representing that a predetermined level force applied on the delivery device 22 has been met or exceeded at the location in which the feedback indicator 36a-b, 60, 74 is incorporated into the delivery device 22. In addition or alternatively, feedback indicators can be provided in a delivery device for other purposes including indicating shipping and handling damage or as a means for identifying a genuine product as compared to a counterfeit delivery device, for example.

As referred to herein, stented transcatheter prosthetic heart valves that are useful with and/or as part of the various systems, devices, and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example. The stented prosthetic heart valves of the present disclosure may be self-expandable, balloon expandable and/or mechanically expandable or combinations thereof. In general terms, the stented prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from, or being forced from, a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

With the above understanding in mind, one simplified, non-limiting example of a stented prosthetic heart valve 100 useful with systems, devices and methods of the present disclosure is illustrated in FIG. 2. As a point of reference, the prosthetic heart valve 100 is shown in a normal or expanded condition in the view of FIG. 2. The prosthetic heart valve 100 includes the stent or stent frame 102 and a valve structure 104.

The stent frame 102 can assume any of the forms mentioned above, and is generally constructed so as to be self-expandable from the compressed condition to the normal, expanded condition (FIG. 2) in some embodiments. In other embodiments, the stent frame 102 is expandable to the expanded condition.

The valve structure 104 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 104 can be formed, for example, from bovine, porcine, equine, ovine and/or other suitable animal tissues. In some embodiments, the valve structure 104 can be formed, for example, from heart valve tissue, pericardium, and/or other suitable tissue. In some embodiments, the valve structure 104 can include or form one or more leaflets 106. For example, the valve structure 104 can be in the form of a tri-leaflet bovine pericardium valve, a bi-leaflet valve, or another suitable valve. In some constructions, the valve structure 104 can comprise two or three leaflets that are fastened together at enlarged lateral end regions to form commissural joints, with the unattached edges forming coaptation edges of the valve structure 104. The leaflets 106 can be fastened to a skirt that in turn is attached to the stent frame 102. The upper ends of the commissure points can define an outflow portion 108 corresponding to a first or outflow end 110 (forcing out fluid) of the prosthesis 100. The opposite end of the valve 104 can define an inflow portion 112 corresponding to a second or inflow end 114 (receiving fluid) of the prosthesis 100. As shown, the stent frame 102 can have a lattice or cell-like structure, and optionally forms or provides crowns or paddles 116 and/or eyelets 118 (or other shapes) at the outflow and inflow ends 110, 114.

The delivery devices shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The device will further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter assembly is delivered through a percutaneous opening in the patient via the delivery device. Once the stented prosthetic heart valve is properly positioned, the balloon catheter is operated to inflate the balloon, thus transitioning the stented prosthetic heart valve to an expanded state.

Although the present disclosure has been described with reference to preferred embodiments, workers skilled in the art will recognize that changes can be made in form and detail without departing from the spirit and scope of the present disclosure. For example, while the devices and systems of the present disclosure have been described as being useful for delivering a stented prosthetic heart valve, a number of other implantable devices can be employed.

What is claimed is:

1. A delivery device for implanting a stented prosthetic heart valve, the delivery device comprising:
   an inner shaft assembly configured for temporary connection with the stented prosthetic heart valve in a loaded state;
   a delivery sheath assembly having an outer sheath that is co-axially received over the inner shaft assembly and including a capsule configured to contain the stented prosthetic heart valve in the loaded state;
   a handle assembly interconnected to the delivery sheath assembly, wherein the handle assembly includes an actuation mechanism for controlling movement of the capsule; and
   a piezochromatic feedback indicator incorporated into the delivery device, wherein at least part of a force provided by the actuation mechanism is translated to the piezochromatic feedback indicator.

2. The delivery device of claim 1, wherein the feedback indicator is positioned in the handle assembly; wherein the feedback indicator visually indicates a level of force exerted on a drive screw element of the handle assembly.

3. The delivery device of claim 1, wherein the piezochromatic feedback indicator includes revisable piezochromatic pigments in that the piezochromatic pigments will change color upon the application of pressure and return to the pigment's original color when the pressure is relieved.

4. The delivery device of claim 1, wherein the piezochromatic feedback indicator includes irreversible piezochromatic pigments; in that the irreversible piezochromatic pigments will change color upon the application of pressure and will not return to the pigment's original color when the pressure is relieved.

5. The delivery device of claim 4, wherein the piezochromatic feedback indicator is arranged and configured to indicate whether the delivery device has been used.

6. The delivery device of claim 1, further comprising a plurality of piezochromatic feedback indicators; wherein the plurality of feedback indicators are separate and distinct components of the delivery device.

7. The delivery device of claim 1, further comprising a plurality of piezochromatic feedback indicators; wherein the plurality of piezochromatic feedback indicators includes at least two of: a first feedback indicator including a reversible piezochromatic pigment, a second feedback indicator including a memory piezochromatic pigment and a third feedback indicator including an irreversible piezochromatic pigment.

8. The delivery device of claim 1, wherein the piezochromatic feedback indicator is dispersed within one of a first material of the handle; a second material of the outer sheath and a third material of the capsule.

9. A delivery device for implanting a stented prosthetic heart valve, the delivery device comprising:
   an inner shaft assembly configured for temporary connection with the stented prosthetic heart valve in a loaded state;
   a delivery sheath assembly configured to contain the stented prosthetic heart valve in the loaded state;
   a handle assembly interconnected to the delivery sheath assembly, the handle including an actuation mechanism for controlling movement of the outer sheath assembly; and
   a piezochromatic feedback indicator proximate the actuating mechanism; wherein at least part of a force provided by the actuation mechanism is translated to the piezochromatic feedback indicator.

10. A delivery device for implanting a stented prosthetic heart valve, the delivery device comprising:
    an inner shaft assembly configured for temporary connection with the stented prosthetic heart valve in a loaded state;
    a delivery sheath assembly having an outer sheath that is co-axially received over the inner shaft assembly and including a capsule configured to contain the stented prosthetic heart valve in the loaded state;
    a handle assembly interconnected to the delivery sheath assembly; and
    a piezochromatic feedback indicator incorporated into the delivery device, wherein the feedback indicator is positioned in the handle assembly and wherein the feedback indicator visually indicates a level of force exerted on a drive screw element of the handle assembly.

* * * * *